US012601721B2

(12) United States Patent
Xie et al.

(10) Patent No.: US 12,601,721 B2
(45) Date of Patent: Apr. 14, 2026

(54) TEST KIT AND DETECTION METHOD FOR ISOTHIAZOLINONES IN TEXTILES

(71) Applicant: Shenzhen Customs Industrial Products Testing Technology Center, Guangdong (CN)

(72) Inventors: Tangtang Xie, Guangdong (CN); Junfeng Lin, Guangdong (CN); Chengfa Li, Guangdong (CN); Chengyun Wang, Guangdong (CN); Yanhua Li, Guangdong (CN); Jiali Zhang, Guangdong (CN)

(73) Assignee: Shenzhen Customs Industrial Products Testing, Shenzhen (CN)

( * ) Notice: Subject to any disclaimer, the term of this patent is extended or adjusted under 35 U.S.C. 154(b) by 784 days.

(21) Appl. No.: 17/952,344

(22) Filed: Sep. 26, 2022

(65) Prior Publication Data

US 2024/0094174 A1 Mar. 21, 2024

(30) Foreign Application Priority Data

Nov. 19, 2021 (CN) ......................... 202111366345.5

(51) Int. Cl.
*G01N 1/34* (2006.01)
*G01N 1/44* (2006.01)
*G01N 31/16* (2006.01)
*G01N 31/18* (2006.01)
*G01N 33/36* (2006.01)

(52) U.S. Cl.
CPC ............... *G01N 31/16* (2013.01); *G01N 1/34* (2013.01); *G01N 1/44* (2013.01); *G01N 31/18* (2013.01); *G01N 33/36* (2013.01)

(58) Field of Classification Search
CPC ............ G01N 31/16; G01N 1/34; G01N 1/44; G01N 31/18; G01N 33/36
See application file for complete search history.

(56) References Cited

FOREIGN PATENT DOCUMENTS

CN 104991003 A * 10/2015

OTHER PUBLICATIONS

Cosmetic preservatives—Mixture of methylchloroisothiazolinone and methylisothiazolinone with magnesium chloride and magnesium nitrate, National Standard of the People's Republic of China, Sep. 6, 2013, GB/T 29666-2013.
Water treatment chemicals—Isothiazolinones, Chemical Industry Standard of the People's Republic of China, Apr. 23, 2008, HG/T 3657-2008.
Determination of methylisothiazolinone and chloromethylisothiazolinone in cosmetics for import and export—Liquid chromatography, Entry-Exit Inspection and Quarantine Industry Standard of the People's Republic of China, Jul. 17, 2008, SN/T 2106-2008.
Determination of 2-methyl-4-isothiazolin-3-one and its derivatives in toys, Entry-Exit Inspection and Quarantine Industry Standard of the People's Republic of China, Sep. 2, 2009, SN/T 2404-2009.

* cited by examiner

*Primary Examiner* — Jill A Warden
*Assistant Examiner* — Michael Stanley Gzybowski

(57) ABSTRACT

The present invention relates to the field of product quality analysis, and specifically, a test kit and detection method for testing isothiazolinone in textiles. A pretreatment step of the present invention adopts a unique process, which may fully transfer isothiazolinone to an acetone and water mixed solution, so that a more accurate measurement result can be achieved. The testing method of the present invention dose not add indicators, does not use large-scale analysis instruments, and is accurate in measurement, easy in reaction termination determination, high in accuracy, low in cost, and strong in popularization and application.

10 Claims, No Drawings

TEST KIT AND DETECTION METHOD FOR ISOTHIAZOLINONES IN TEXTILES

CROSS-REFERENCE TO RELATED APPLICATION

The present application claims priority from Chinese Patent Application No. 202111366345.5 filed on Nov. 19, 2021, the contents of which are incorporated herein by reference in their entirety.

TECHNICAL FIELD

The present invention relates to the field of product quality analysis, and specifically, a test kit and detection method for pretreating and detecting isothiazolinone content in textiles.

BACKGROUND

Isothiazolinone compound as antibacterial agent is mainly composed of an isothiazolinone ring, which is the general name for a series of isothiazolinone derivatives. As a novel industrial antibacterial agent, the compound is widely applicable to many fields such as textile, printing, dyeing and coating, paper making, agriculture and forestry environment protection. The isothiazolinone antibacterial agent plays more and more important role in daily work and industry due to the advantages of being work efficient, environmentally friendly and broad-spectrum antibacterial. On Apr. 21, 2010, the notification "Consumer Product Safety Standard Proposal" (No. G/TBT/N/KOR/270) issued by the Korean Agency for Technology and Standards (KATS), adds an allowable limit standard of 10 harmful compounds in fabric finishing agent, such as methylisothiazolinone, phenoxyethanol and isothiazolinone. European Union Regulations EU 2015/2016 and EU 2015/2017 provided the restriction of CMIT and MIT mixtures, in which the limits of CMIT, MIT, BIT in water-based toys are 1.0, 0.75, 0.25 and 5.0 mg/kg. The European Union Biocidal Products Regulation (BPR, No 528/2012) has successively included MIT, CMIT, BIT, MBIT, BBIT, OIT and DCOIT as restricted preservatives in textile, leather, rubber and polymeric materials. In some research literatures, certain isothiazolinones have significant contact sensitization and can cause contact dermatitis.

The detection methods for isothiazolinones finishing agent have been reported, includes: Chinese National Standards GB/T 41559-2022 Textiles—Determination of isothiazolone compound, GB/T 29666-2013 Cosmetic preservatives—Mixture of methylchloroisothiazolinone and methylisothiazolinone with magnesium chloride and magnesium nitrate, and European Union Standards EN 71-11 Safety of toys Organic chemical compounds: Methods of analysis. Most of the above methods are instrumental analysis methods, which are complex in operation and high in cost.

SUMMARY

The present invention is intended to provide a method for pretreating isothiazolinones in textiles, and a rapid and simple chemical analysis kit and method of isothiazolinones content.

In order to achieve the above objective, the present invention provides a method for obtaining the pretreated acetone and water mixed solution containing isothiazolinones includes the following steps.

(1) The textile sample is cut into pieces. A certain mass of tested pieces are accurately weighed.

(2) The pieces obtained in step (1) are heated to 30-60° C., then the pieces are placed in an environment with the vacuum degree being 0.060-0.080 MPa for 15-30 min, and low boiling point organics affecting measurement are removed.

(3) The pieces obtained in step (2) are mixed with the acetone and water mixed solution with a mass ratio of 10-15 times, then the mixed solution is heated, and the solution temperature is maintained at about 35° C. for 15-30 min.

(4) Sonicate is performed in the mixed solution obtained in step (3) in an ultrasonic wave for 5 min, in order to cause isothiazolinones in textiles to be fully transferred to the acetone and water mixed solution.

(5) The solution obtained in step (4) is filtered with a filter paper, the pieces are washed with water. Both filtrated stock solution and washed solution are collected, to obtain isothiazolinones in the pretreated acetone and water mixed solution.

Further, in the acetone and water mixed solution, the volume ratio of acetone to water is 15-3:1.

Further, the heating temperature of the pieces in step (2) is 45-55° C., and the vacuum degree is 0.070-0.075 MPa.

Impurities affecting measurement result may be removed by using the pretreatment step of the present invention. In addition, since acetone solvent with good solubility is used, 98% isothiazolinone in a test sample may be transferred to the acetone and water mixed solution in one treatment.

Further, the method for rapidly detecting isothiazolinones by using the prepared acetone and water mixed solution, including the following steps.

Step 1: A pretreated acetone and water mixed solution containing isothiazolinones is transferred to a 25 mL volumetric flask, to make up to volume.

Step 2: 10 mL of the above volume solution is measured and transferred to a reaction vessel, then 0.5-1 g of an acidic material is added. After closing, uniform stirring is performed. A potassium permanganate standard solution is added to a microburette, then titration is started. There is a reaction terminates when the solution color changes from colorless to light fuchsia and does not fade within half a minute.

Step 3: The content of the isothiazolinone is calculated according to the volume of potassium permanganate standard solution consumed in step 2 and the molar ratio of isothiazolinone to potassium permanganate during reaction.

Further, the concentration of the potassium permanganate standard solution is 0.001-0.1 mol/L.

Further, the acidic material is a mixed compound of one or two of a sulfuric acid solution, sodium bisulfate, and benzenesulfonic acid with a mass concentration being 15-70%.

Further, a calculation formula of the number n of moles of isothiazolinones is shown as follows.

$n=C_{standard\ solution}\times V_{standard\ solution}\div 1000\div N_{potassium\ permanganate}\times N_{isothiazolinone}\div 10\times 25$, where n is the number n of moles of isothiazolinones, mol; $C_{standard\ solution}$ is the concentration of the potassium permanganate standard solution, in mol/L; $V_{standard\ solution}$ is the volume of the potassium permanganate standard solution that titration consumes, in mL; $N_{potassium\ permanganate}$ is the stoichiometric coefficient of potassium permanganate during reaction; $N_{isothiazolinone}$ is the stoichiometric coefficient of isothiazolinone during reaction; 25 is filled volume; and 10 is weighed volume from the filled solution.

Further, a calculation formula of the content of isothiazolinones ($X_1$ or $X_2$) is shown as follows.

$X_1$=n×M÷m×$10^6$, $X_2$=n÷m×$10^3$, where $X_1$ is the content of isothiazolinones, in mg/kg; $X_2$ is the content of isothiazolinones, in mol/kg; n is the number of moles of the isothiazolinone, in mol; M is the molar mass of the isothiazolinone, in g/mol; and m is the mass of accurately weighed textile, in g. When there is a mixture of isothiazolinones, n is the sum of the numbers of moles of all isothiazolinones, and M is the average molar mass of all isothiazolinones.

The present invention further provides a test kit for detecting the isothiazolinones content, including at least: an acidic material and a potassium permanganate standard solution.

Further, the acidic material is a mixed compound of one or two of a sulfuric acid solution, sodium bisulfate, and benzenesulfonic acid with a mass concentration being 15-70%.

A pretreatment step of the present invention adopts a unique process. Isothiazolinones in a test sample may be fully extracted to an acetone and water mixed solution, and extraction efficiency reaches 98%. Therefore, the more accurate measurement result can be achieved. The testing method of the present invention dose not add indicators, does not use large-scale analysis instruments, and is accurate in measurement, easy in reaction termination determination, high in accuracy, low in cost, and strong in application. Limited by the accuracy reading of the microburette and the concentration of the potassium permanganate solution, the content ranges of isothiazolinones in textiles of this kit and detection method provided in the present invention is from 1 to 10000 mg/kg or $1\times10^{-5}$ to 0.1 mol/kg.

DETAILED DESCRIPTION OF THE EMBODIMENTS

The technical solutions in the embodiments of the present invention are clearly and completely described below. It is apparent that the described embodiments are only part of the embodiments of the present invention, not all the embodiments. Based on the embodiments in the present invention, all other embodiments obtained by those of ordinary skilled in the art without creative work shall fall within the protection scope of the present invention.

It should be understood that the specific embodiments described here are merely used to explain the present invention, and are not used to limit the present invention.

Embodiment 1

A method for pretreating 5-chloro-2-methyl-4-isothiazolin-3-one (CMI) in a cotton textile includes the following steps.

(1) The cotton sample is cut into pieces. 1.345 g of tested pieces are accurately weighed.

(2) The pieces obtained in step (1) are heated to 30-35° C., then the pieces are placed in an environment with the vacuum degree being 0.060-0.065 MPa for 15-30 min, and low boiling point organics affecting measurement are removed.

(3) The pieces obtained in step (2) are mixed with the acetone and water mixed solution with a mass ratio of 10 times, in which a volume ratio of acetone to water is 3:1, then the mixed solution is heated, and the solution temperature is maintained at about 35° C. for 15 min.

(4) Sonicate is performed in the mixed solution obtained in step (3) in an ultrasonic wave for 5 min, in order to cause the CMI therein to be fully transferred to the acetone and water mixed solution.

(5) The solution obtained in step (4) is filtered with a filter paper, the pieces are washed with water. Both filtrated stock solution and washed solution are collected, to obtain the CMI in the pretreated acetone and water mixed solution.

A method for measuring the CMI content by using the prepared acetone and water mixed solution containing the CMI includes the following steps.

(6) A pretreated acetone and water mixed solution containing the CMI obtained in step (5) is transferred to a 25 mL volumetric flask, to make up to volume.

(7) 10 mL of the above solution obtained in step (6) is measured and transferred to a reaction vessel, then 0.5 g of a sulfuric acid solution with a mass concentration being 25% is added. After closing, uniform stirring is performed, 0.001 mol/L of the potassium permanganate standard solution is added to a microburette, then titration is started. 0.32 mL of the potassium permanganate standard solution is consumed when the solution color changes from colorless to light fuchsia and does not fade within half a minute.

(8) The content of the isothiazolinone is calculated according to the volume of potassium permanganate standard solution consumed in step (7) and the molar ratio of isothiazolinone to potassium permanganate during reaction.

Chemical reactions of the above analysis method include the following.

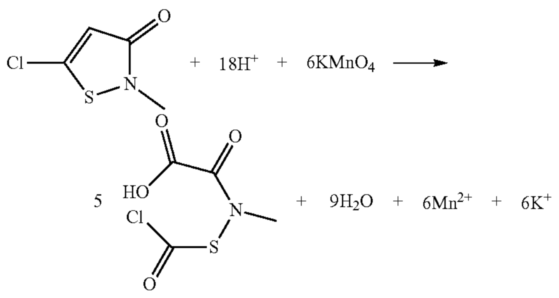

A calculation formula of the number n of moles of the CMI is shown as follows.

$$n=C_{standard\ solution}\times V_{standard\ solution}\div1000\div N_{potassium\ permanganate}\times N_{isothiazolinone}\div10\times25=0.001\times0.32\div1000\div6\times5\div10\times25=7.5\times10^{-8}\ \text{mol.}$$

A calculation formula of the content $X_1$ or $X_2$ of the CMI is shown as follows.

$$X_1=n\times M\div m\times10^6=7.5\times10^{-8}\times149\div1.345\times10^6=8.31\ \text{mg/kg.}$$

$$X_2=n\div m\times10^3=7.5\times10^{-8}\div1.345\times10^3=5.57\times10^{-5}\ \text{mol/kg.}$$

A sample is taken from 15 mL of the remaining sample in the volumetric flask in the step (6), and is measured by a common high-performance liquid chromatography; and a CMI measuring result is 8.31 mg/kg, which is comparable to a measurement result of the present invention and is high in accuracy.

Embodiment 2

A method for pretreating 2-methyl-4-isothiazolin-3-one (MI) in a silk-containing textile includes the following steps.

(1) The cotton sample is cut into pieces. 1.500 g of tested pieces are accurately weighed.

(2) The pieces obtained in step (1) are heated to 45-55° C., the pieces are placed in an environment with a vacuum degree being 0.070-0.078 MPa for 30 min, and low boiling point organics affecting measurement are removed.

(3) The pieces obtained in step (2) are mixed with the acetone and water mixed solution with a mass ratio of 10 times, a volume ratio of acetone to water is 15:1, then the mixed solution is heated, and a temperature is maintained at about 35° C. for 30 min.

(4) Sonicate is performed in the mixed solution obtained in step (3) in an ultrasonic wave for 5 min, in order to cause the MI therein to be fully transferred to the acetone and water mixed solution.

(5) The solution obtained in step (4) is filtered with a filter paper, the pieces are washed with water. Both the filtrated stock solution and washed solution are collected, to obtain the MI in the pretreated acetone and water mixed solution.

A method for measuring the content of the MI by using the prepared acetone and water mixed solution containing the MI includes the following steps.

(6) A pretreated acetone and water mixed solution containing the MI obtained in step (5) is transferred to a 25 mL volumetric flask, to make up to volume.

(7) 10 mL of the above solution obtained in step (6) is measured and transferred to a reaction vessel, 0.8 g of benzenesulfonic acid is added. After closing, uniform stirring is performed, 0.002 mol/L of the potassium permanganate standard solution is added to a microburette, then titration is started, and 0.11 mL of the potassium permanganate standard solution is consumed when the solution color changes from colorless to light fuchsia and does not fade within half a minute.

(8) The content of the isothiazolinone is calculated according to the volume of potassium permanganate standard solution consumed in step (7) and the molar ratio of isothiazolinone to potassium permanganate during reaction.

Chemical reactions of the above analysis method include the following.

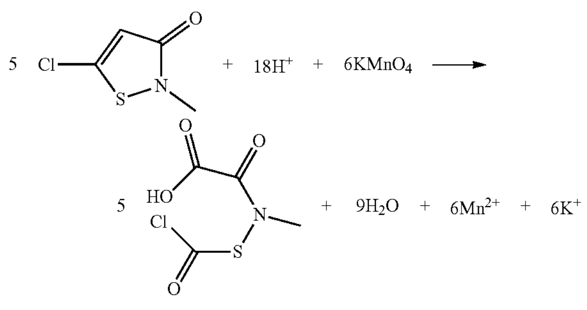

By adopting the calculation method of Embodiment 1, the following may be obtained.

$$X_1=n\times M\div m\times 10^6=13.65\ \text{mg/kg}.$$

$$X_2=n\div m\times 10^3=9.17\times 10^{-5}\ \text{mol/kg}.$$

A sample is taken from 15 mL of the remaining sample in the volumetric flask in the step (6), and is measured by a common high-performance liquid chromatography; and an MI measuring result is 13.94 mg/kg, which is comparable to a measurement result of the present invention and is high in accuracy.

Embodiment 3

A method for pretreating the CMI and the MI in a polyester-containing textile includes the following steps.

(1) The cotton sample is cut into pieces. 2.123 g of tested pieces is accurately weighed.

(2) The pieces obtained in step (1) are heated to 30-38° C., then the pieces are placed in an environment with a vacuum degree being 0.070-0.075 MPa for 30 min, and low boiling point organics affecting measurement are removed.

(3) The pieces obtained in step (2) are mixed with the acetone and water mixed solution with a mass ratio of 10 times, a volume ratio of acetone to water is 9:1, then the mixed solution is heated, and a temperature is maintained at about 35° C. for 30 min.

(4) Sonicate is performed in the mixed solution obtained in step (3) in an ultrasonic wave for 5 min, in order to cause the CMI and MI therein to be fully transferred to the acetone and water mixed solution.

(5) The solution obtained in step (4) is filtered with a filter paper, the pieces are washed with water. Both the filtrated stock solution and washed solution are collected, to obtain the CMI and MI in the pretreated acetone and water mixed solution.

A method for measuring the sum content of the CMI and MI by using the prepared acetone and water mixed solution containing the CMI and MI includes the following steps.

(6) A pretreated acetone and water mixed solution containing the CMI and MI obtained in step (5) is transferred to a 25 mL volumetric flask, to make up to volume.

(7) 10 mL of the aboved solution obtained in step (6) is measured and transferred to a reaction vessel, then 1 g of sodium bisulfate is added. After closing, uniform stirring is performed, 0.080 mol/L of the potassium permanganate standard solution is added to a microburette, then titration is started, and 0.38 mL of the potassium permanganate standard solution is consumed when the solution color changes from colorless to light fuchsia and does not fade within half a minute.

(8) The content of the isothiazolinone is calculated according to the volume of potassium permanganate standard solution consumed in step (7) and the molar ratio of isothiazolinone to potassium permanganate during reaction.

By adopting the calculation methods of Embodiment 1 and Embodiment 2, the following may be obtained.

$X_1=n\times M_{average}\div m\times 10^6=1350.9$ mg/kg, and $M_{average}$ is an average molar mass of the CMI and the MI.

$X_2=n_{average}\div m\times 10^3=1.02\times 10^{-2}$ mol/kg.

A sample is taken from 15 mL of the remaining sample in the volumetric flask in the step (6), and is measured by a common high-performance liquid chromatography; and the sum content between CMI and MI is 1309.4 mg/kg, which is comparable to a measurement result of the present invention and is high in accuracy.

In order to verify the accuracy of the method in the present invention, the recovery rate and Relative Standard Deviation (RSD) of textiles with different substrates are tested, and results are shown as follows.

The cotton-containing textile and silk-containing textile without isothiazolinone are used as blanks; standard samples with concentration levels being 3 mg/kg, 6 mg/kg and 9 mg/kg are respectively added; 5 samples are prepared for each concentration level; the recovery rate and RSD are inspected; and results are shown in Table 1 and Table 2.

TABLE 1

Recovery rate and RSD of cotton-containing textile

| | Addition level | Recovery rate (%) CMI | MI | CMI + MI |
|---|---|---|---|---|
| Blank cotton-containing textile | 3 mg/kg | 96.02 | 95.19 | 97.19 |
| | | 95.41 | 94.29 | 91.38 |
| | | 92.28 | 93.85 | 97.45 |
| | | 96.21 | 95.29 | 90.10 |
| | | 91.42 | 91.19 | 90.27 |
| | Mean value | 94.27 | 93.96 | 93.28 |
| | RSD | 2.13 | 1.58 | 3.57 |
| | 6 mg/kg | 98.19 | 96.21 | 90.28 |
| | | 92.34 | 95.24 | 99.10 |
| | | 99.10 | 99.21 | 89.62 |
| | | 94.30 | 93.67 | 90.21 |
| | | 98.21 | 90.28 | 91.29 |
| | Mean value | 96.43 | 94.92 | 92.10 |
| | RSD | 2.73 | 3.10 | 3.84 |
| | 9 mg/kg | 98.01 | 98.42 | 98.21 |
| | | 92.21 | 99.21 | 90.28 |
| | | 93.46 | 90.67 | 95.21 |
| | | 95.21 | 94.54 | 99.23 |
| | | 90.65 | 90.54 | 87.23 |
| | Mean value | 93.91 | 94.68 | 94.03 |
| | RSD | 2.70 | 3.89 | 4.90 |

TABLE 2

Recovery rate and RSD of silk-containing textile

| | Addition level | Recovery rate(%) CMI | MI | CMI + MI |
|---|---|---|---|---|
| Blank silk-containing textile | 3 mg/kg | 94.21 | 91.67 | 101.40 |
| | | 93.21 | 91.29 | 90.21 |
| | | 94.79 | 93.89 | 92.41 |
| | | 97.09 | 94.27 | 91.34 |
| | | 90.25 | 94.21 | 89.47 |
| | Mean value | 93.91 | 93.07 | 92.97 |
| | RSD | 2.37 | 1.40 | 4.66 |
| | 6 mg/kg | 95.21 | 96.78 | 99.18 |
| | | 93.33 | 93.56 | 99.90 |
| | | 92.19 | 91.34 | 91.71 |
| | | 94.56 | 96.58 | 91.67 |
| | | 94.21 | 91.52 | 97.88 |
| | Mean value | 93.90 | 93.96 | 96.07 |
| | RSD | 1.12 | 2.51 | 3.78 |
| | 9 mg/kg | 91.21 | 92.17 | 98.99 |
| | | 92.30 | 92.46 | 91.27 |
| | | 94.65 | 90.60 | 88.68 |
| | | 94.29 | 95.55 | 103.25 |
| | | 92.10 | 97.41 | 96.30 |
| | Mean value | 92.91 | 93.64 | 95.70 |
| | RSD | 1.43 | 2.64 | 5.47 |

The above data show that, the testing method of the present invention has good recovery rate and RSD values for single isothiazolinone. The recovery rate and RSD values of the testing method of the present invention are slightly poor for the mixture of the isothiazolinone, but are still comparable to recovery rate and RSD values of high-performance liquid chromatography, so that the testing method has high promotion and application values.

The above descriptions are merely the preferred embodiments of the present invention, and are not intended to limit the scope of the present invention. Any equivalent transformation made by the description of the present invention under the concept of the present invention, or directly/indirectly applied in other related technical fields are all included in the scope of patent protection of the present invention.

What is claimed is:

1. A method for obtaining pretreated isothiazolinones in an acetone and water mixed solution from textiles, comprising the following steps:

(1) cutting textiles to be tested into pieces, accurately weighing a certain mass of the pieces;

(2) heating the pieces obtained in step (1) to 30-60° C., then placing the pieces in an environment with a vacuum degree being 0.060-0.080 MPa for 15-30 min, and removing low boiling point organics affecting measurement;

(3) mixing the pieces obtained in step (2) and an acetone and water mixed solution with a mass ratio of 10-15 times, then heating the mixed solution, and maintain a temperature at about 35° C. for 15-30 min;

(4) performing sonicate in the mixed solution obtained in step (3) in an ultrasonic wave for 5 min, in order to cause isothiazolinones in textiles to be fully transferred to the acetone and water mixed solution; and (5) filtering the solution obtained in step (4) with a filter paper, washing the pieces with water, and mixing both filtrated solution and washed solution, to obtain pretreated isothiazolinones in the acetone and water mixed solution.

2. The method as claimed in claim 1, wherein in the acetone and water mixed solution, a volume ratio of acetone to water is 15-3:1.

3. The method as claimed in claim 1, wherein the heating temperature of the pieces in step (2) is 45-55° C., and the vacuum degree is 0.070-0.075 MPa.

4. A method for rapidly detecting isothiazolinone in textiles, comprising the following steps:

step 1, transferring pretreated isothiazolinones in an acetone and water mixed solution obtained by the method as claimed in claim 1 to a 25 mL volumetric flask, making the mixed solution to have a volume of 25 mL to obtain a standard solution;

step 2, measuring 10 mL of the above standard solution, adding 0.5-1 g of an acidic material, performing uniform stirring, adding a potassium permanganate standard solution to a microburette, then starting titration, and determining that a reaction terminates after the solution changes from colorless to pale fuchsia and does not fade within half a minute; and step 3, calculating the content of the isothiazolinone according to a volume of the potassium permanganate standard solution consumed in step 2 and a molar ratio of the isothiazolinone to potassium permanganate during reaction.

5. The method for measuring the content of isothiazolinones as claimed in claim 4, wherein the concentration of the potassium permanganate standard solution is 0.001-1 mol/L.

6. The method for measuring the content of isothiazolinones as claimed in claim 4, wherein the acidic material is a mixed compound of one or two of a sulfuric acid solution, sodium bisulfate, and benzenesulfonic acid with a mass concentration being 15-70%.

7. The method for measuring the content of isothiazolinone as claimed in claim 4, wherein a calculation formula of the number n of moles of the isothiazolinone is:

$n=C_{standard\ solution}\times V_{standard\ solution}=1000\div N_{potassium\ permanganate}\times N_{isothiazolinone}\div 10\times 25$, wherein the unit of n is mol; $C_{standard\ solution}$ is the concentration of the potassium permanganate standard solution, in mol/L; $V_{standard\ solution}$ is the volume of the potassium permanganate standard solution that titration consumes, in mL; $N_{potassium\ permanganate}$ is a stoichiometric coefficient of the potassium permanganate during reaction; $N_{isothiazolinone}$ is a stoichiometric coefficient of the isothiazolinone during reaction; 25 is a constant volume; and 10 is a volume weighed after making the mixed solution to have a volume of 25 mL.

8. The method for measuring the content of isothiazolinone as claimed in claim 4, wherein a calculation formula of the content $X_1$ or $X_2$ of the isothiazolinone is:

$X_1=n\times M\div m\times 10^6$, $X_2=n\div m\times 10^3$, wherein the unit of $X_1$ is mg/kg; the unit of $X_2$ is mol/kg; n is the number of moles of the isothiazolinone, in mol; M is a molar mass of the isothiazolinone, in g/mol; and m is the mass of accurately weighed textile, in g; and when the isothiazolinone is a mixture, n is a sum of the numbers of moles of all of the isothiazolinone, and M is an average molar mass of all of the isothiazolinone.

9. A method for rapidly detecting isothiazolinone in textiles, comprising the following steps:

step 1, transferring pretreated isothiazolinones in an acetone and water mixed solution obtained by the method as claimed in claim 2 to a 25 mL volumetric flask, making the mixed solution to have a volume of 25 mL to obtain a standard solution;

step 2, measuring 10 mL of the above standard solution, adding 0.5-1 g of an acidic material, after closing, performing uniform stirring, adding a potassium permanganate standard solution to a microburette, then starting titration, and determining that a reaction terminates after the solution changes from colorless to light fuchsia and does not fade within half a minute; and step 3, calculating the content of the isothiazolinone according to a volume of the potassium permanganate standard solution consumed in step 2 and a molar ratio of the isothiazolinone to potassium permanganate during reaction.

10. A method for rapidly detecting isothiazolinone in textiles, comprising the following steps:

step 1, transferring pretreated isothiazolinones in an acetone and water mixed solution obtained by the method as claimed in claim 3 to a 25 mL volumetric flask, to make up to volume making the mixed solution to have a volume of 25 mL to obtain a standard solution;

step 2, measuring 10 mL of the above standard solution, adding 0.5-1 g of an acidic material, after closing, performing uniform stirring, adding a potassium permanganate standard solution to a microburette, then starting titration, and determining that a reaction terminates after the solution changes from colorless to light fuchsia and does not fade within half a minute; and step 3, calculating the content of the isothiazolinone according to a volume of the potassium permanganate standard solution consumed in step 2 and a molar ratio of the isothiazolinone to potassium permanganate during reaction.

* * * * *